US006793973B2

(12) United States Patent
Winterton et al.

(10) Patent No.: US 6,793,973 B2
(45) Date of Patent: Sep. 21, 2004

(54) SINGLE-DIP PROCESS FOR ACHIEVING A LAYER-BY-LAYER-LIKE COATING

(75) Inventors: Lynn Cook Winterton, Alpharetta, GA (US); John Martin Lally, Lilburn, GA (US); Michael Rubner, Westford, ME (US); Yongxing Qiu, Duluth, GA (US)

(73) Assignee: Novartis AG, Basel (CH)

( * ) Notice: Subject to any disclaimer, the term of this patent is extended or adjusted under 35 U.S.C. 154(b) by 603 days.

(21) Appl. No.: 09/775,104

(22) Filed: Feb. 1, 2001

(65) Prior Publication Data

US 2001/0048975 A1 Dec. 6, 2001

Related U.S. Application Data

(60) Provisional application No. 60/180,463, filed on Feb. 4, 2000.

(51) Int. Cl.[7] .................................................. B05D 1/34
(52) U.S. Cl. ................................ 427/393.5; 427/412.1
(58) Field of Search .......................... 427/393.5, 412.1

(56) References Cited

U.S. PATENT DOCUMENTS

| | | | |
|---|---|---|---|
| 4,168,112 A | 9/1979 | Ellis et al. | 351/160 |
| 4,321,261 A | 3/1982 | Ellis et al. | 424/180 |
| 4,941,997 A | 7/1990 | Decher et al. | 252/586 |
| 4,973,429 A | 11/1990 | Decher et al. | 252/587 |
| 5,068,318 A | 11/1991 | Decher et al. | 534/573 |
| 5,518,767 A | 5/1996 | Rubner et al. | 427/259 |
| 5,529,727 A | 6/1996 | LaBombard | 264/1.36 |
| 5,536,573 A | 7/1996 | Rubner et al. | 428/378 |
| 6,011,082 A | 1/2000 | Wang | 523/107 |
| 6,020,175 A | 2/2000 | Onda et al. | 435/180 |
| 6,451,871 B1 * | 9/2002 | Winterton et al. | 523/106 |

FOREIGN PATENT DOCUMENTS

| | | |
|---|---|---|
| EP | 0 032 443 A2 | 1/1981 |
| EP | 0 138 385 A | 4/1985 |
| GB | 2012070 | 1/1978 |
| JP | 01158412 | 2/1980 |
| WO | WO 95/00618 | 1/1995 |
| WO | WO 95/02251 | 1/1995 |
| WO | WO 95/20407 | 8/1995 |
| WO | WO 96/37241 | 4/1996 |
| WO | WO 96/18498 | 6/1996 |
| WO | WO 96/31792 | 10/1996 |
| WO | WO 99 35520 A | 7/1999 |
| WO | WO 01 27209 A | 4/2001 |

OTHER PUBLICATIONS

Sun et al, Langmuir, 16(10), pp 4620–4624, 2000.*
Cho et al, Korean Journal of Chemical Engineering, 20(1), pp 174–179, 2003.*

Blood Capatibility–Surface Characteristic Relationships of a Langmuir–Blodgett Film Composed of an Anionic Amphiphile–Polycation Complex, Uchida M., et al., New Polymers Material, vol. 4, No. 3 pp. 119–211 (1994).

Enhancement of Light Emitting Diodes Based on Self–Assembled Heterosctructures of Poly (P–phenylene vinylene), O. Onitsuka, et al., Journal Applied Physics, 80, (7), Oct. 1, 1996, ppg 4067–4071.

Investigations of New Self–Assembled Multilayer Thin Films Based on Alternately Absorbed Layers of Polyelectrolytes and Functional Dye Molecules, D. Yoo, et al., Material Resource, Soc. Symp. Proc. vol. 413, 1996, Materials Research Society.

New Electro–Active Self–Assembled Multilayer Thin Films Based on Alternately Absorbed Layers of Polyelectrolytes and Functional Dye Molecules, D. Yoo, et al., Elsevier Science, S.A., 1977, ppg 1425–1426.

Layer–By–Layer Modification of Surfaces Through the Use of Self–Assembled Monolayers of Polyions, D. Yoo, et al., ANTEC, 1995 ppg 2568–2570.

Patterned Polymer Multilayer Fabrication by Controlled Adhesion of Polyelectrolytes to Plasma–Modified Fluoropolymer Surfaces, T. G. Vargo, et al, Supramolecular Science, vol. 2, Nos. 3–4, 1995, ppg 169–174.

Molecular–Level Processing of Conjugated Polymers 1. Layer–by–Layer Manipulation of Conjugated Polyions, M. Ferreira, et al., Macromolecules, vol. 28, No. 21, 1995, ppg 7107–7114.

Molecular–Level Processing of Conjugated Polymers 2. Layer–by–Layer Manipulation of In–Situ Polymerized p–type Doped Conductiong Polymers, M. Ferreira, et al., Macromolecules, vol. 28, No. 21, 1995, ppg 7115–7120.

Molecular–Level Processing of Conjugated Polymers 3. Layer–by–Layer Manipulation of of Ppolyaniline via Electrowstatic Interactions, J. H. Cheung, et al., Macromolecules, 1997, 30, ppg 2712–2716.

* cited by examiner

*Primary Examiner*—Erma Cameron
(74) *Attorney, Agent, or Firm*—Jian S. Zhou; Robert J. Gorman; R. Scott Meece

(57) ABSTRACT

A method of forming a coating of polyionic materials in a layer-by-layer-like manner onto a polymeric material is provided. A polymeric material, such as a contact lens, can be dipped once into a solution of polyionic materials such that layers of polyionic material can be formed thereon. A single dip solution of the present invention typically contains a polyanionic material and a polycationic material in a non-stoichiometric amount and maintained within a certain pH range.

31 Claims, No Drawings

SINGLE-DIP PROCESS FOR ACHIEVING A LAYER-BY-LAYER-LIKE COATING

This application claims priority to provisional application 60/180,463 filed Feb. 4, 2000.

FIELD OF THE INVENTION

The present invention generally relates to a method of treating polymeric materials, such as biomedical devices and contact lenses. In particular, the present invention is directed to a method of altering the hydrophobic or hydrophilic nature of the polymeric surface of a biomedical device by applying a single-dip polyionic solution to form a layer-by-layer-like coating thereon.

BACKGROUND OF THE INVENTION

Many devices used in biomedical applications require that the bulk of the device have one property, while the surface of the device has another property. For example, contact lenses may have high oxygen permeability through the lens to maintain good corneal health. However, materials that exhibit exceptionally high oxygen permeability (e.g. polysiloxanes) are typically hydrophobic and will adhere to the eye. Thus, a contact lens generally has a core or bulk material that is highly oxygen permeable and hydrophobic, and a surface that has been treated or coated to increase hydrophilic properties, thereby allowing the lens to freely move on the eye without adhering excessive amounts of tear lipid and protein.

In order to modify the hydrophilic nature of a relatively hydrophobic contact lens material, a contact lens can be treated with a plasma treatment. For example, a high quality plasma treatment technique is disclosed in PCT Publication No. WO 96/31793 to Nicholson et al. Some plasma treatment processes, however, require a significant monetary investment in certain equipment. Moreover, plasma treatment requires that the lens be dry before exposure to the plasma. Thus, lenses that are wet from prior hydration or extraction processes must be dried, thereby imposing added costs of obtaining drying equipment, as well as added time in the overall lens production process. As a result, a number of methods of consistently and permanently altering the surface properties of polymeric biomaterials, such as contact lenses, have been developed. Some of these techniques include Langmuir-Blodgett deposition, controlled spin casting, chemisorptions, and vapor deposition. Useful examples of Langmuir-Blodgett layer systems are disclosed in U.S. Pat. Nos. 4,941,997; 4,973,429; and 5,068,318.

A more recent technique used for coating electronic devices is a layer-by-layer ("LbL") polymer absorption process, which is described in "Investigation of New Self-Assembled Multilayer Thin Films Based on Alternately Adsorbed Layers of Polyelectrolytes and Functional Dye Molecules" by Dongsik Yoo, et al. (1996). The process described in this article involves alternatively dipping hydrophilic glass substrates in a polyelectrolyte solution (e.g., polycations such as polyallylamine or polyethyleneimine) and then in an oppositely charged dye solution to form electrically conducting thin films and light-emitting diodides (LEDs). After each dipping, the substrates are rinsed with acidic aqueous solutions. Both the dipping and rinsing solutions have a pH of 2.5 to 7. Prior to dipping, the surfaces of the glass substrates are treated in order to create a surface having an affinity for the polyelectrolyte.

Similar to the above process, two other processes are described by "Molecular-Level Processing of Conjugated Polymers" by Fou & Rubner and Ferreira & Rubner, respectively. These processes involve treating glass substrates that have hydrophilic, hydrophobic, negatively, or positively charged surfaces. The glass surfaces are treated for extended periods in hot acid baths and peroxide/ammonia baths to produce a hydrophilic surface. Hydrophobic surfaces are produced by gas-phase treatment in the presence of 1,1,1, 3,3,3-hexamethyldisilazane for 36 hours. Charged surfaces are prepared by covalently anchoring charges onto the surface of the hydrophilic slides. For example, positively charged surfaces are made by further treating the hydrophilic surfaces in methanol, methanol/toluene, and pure toluene rinses, followed, by immersion in (N-2 aminoethyl-3-aminopropyl) trimethyloxysilane solution for 12 to 15 hours. This procedure produces glass slides with amine functionalities, which are positively charged at a low pH.

In addition to the above-described techniques, U.S. Pat. Nos. 5,518,767 and 5,536,573 to Rubner et al. describe methods of producing bilayers of p-type doped electrically conductive polycationic polymers and polyanions or water-soluble, non-ionic polymers on glass substrates. These patents describe extensive chemical pre-treatments of glass substrates that are similar to those described in the aforementioned articles.

The methods described above generally relate to layer-by-layer polyelectrolyte deposition. However, these methods require a complex and time-consuming pretreatment of the substrate to produce a surface having a highly charged, hydrophilic, or hydrophobic nature in order to bind the polycationic or polyanionic material to the glass substrate.

To reduce the complexity, costs, and time expended in the above-described processes, a layer-by-layer polyelectrolyte deposition technique was developed that could be effectively utilized to alter the surfaces of various materials, such as contact lenses. This technique is described in co-pending U.S. Patent Application entitled "Apparatus, Methods, and Compositions for Modifying Surface Characteristics". In particular, a layer-by-layer technique is described that involves consecutively dipping a substrate into oppositely charged polyionic materials until a coating of a desired thickness is formed. Nevertheless, although this technique provides an effective polyelectrolyte deposition technique for biomaterials, such as contact lenses, a need for further improvement still remains. For example, with this layer-by-layer dipping process, a coating could require multiple dipping steps that take a substantial amount of time to apply. As a result, manufacturing costs can often be increased due to the amount of time and dipping required to sufficiently coat the substrate.

As such, a need currently exists for an improved method of coating a material, such as a contact lens, with polyelectrolyte (polyionic) layers. In particular, a need exists for an improved polyionic deposition technique that requires less time and dipping than the previously-described layer-by-layer deposition technique.

SUMMARY OF THE INVENTION

Accordingly, an object of the present invention is to provide an improved method of treating polymers, such as ophthalmic lenses, to alter surface properties.

It is another object of the present invention to provide an improved method of treating polymers with polyionic materials to alter the hydrophilic or hydrophobic nature of their surfaces.

Still another object of the present invention is to provide an improved method of coating a polymer substrate with a polyionic material to alter the surface properties of the substrate.

Yet another object of the present invention is to provide an improved method of coating a polymer substrate with a polyanionic and a polycationic material.

Another object of the present invention is to provide a method of coating a polymer substrate with layers of a polyanion and polycation in a relatively short period of time.

It is another object of the present invention to provide a method for applying layers of a polyanion and polycation to a substrate in a single dip.

These and other objects of the present invention are achieved by providing a method for applying a polyionic solution to a substrate material, such as a contact lens. The method of the present invention can, in most embodiments, apply successive layers of polyionic material onto the substrate with only a single dip of the substrate into the polyionic solution.

In accordance with the present invention, a polyionic solution is employed to coat the substrate. In general, the polyionic solution contains at least one polycationic material and at least one polyanionic material, although more than one of each polyionic material can be employed. In one embodiment, for example, the polyionic solution is a bicomponent solution containing a polycation and a polyanion.

Typically, a polycationic material of the present invention can include any material known in the art to have a plurality of positively charged groups along a polymer chain. For example, in one embodiment, the polycationic material includes poly(allyl amine hydrochloride). Likewise, a polyanionic material of the present invention can typically include any material known in the art to have a plurality of negatively charged groups along a polymer chain. For example, in one embodiment, the polyanionic material includes polyacrylic acid.

According to the present invention, a polycationic material is combined with a polyanionic material to form the polyionic solution. In general, the polyionic components are added in non-stoichiometric amounts such that one of the components is present within the solution in a greater amount than another component. In particular, the molar charge ratio, as defined herein, can be from about 3:1 to about 100:1. In certain embodiments, the molar charge ratio is 10:1 (polyanion:polycation).

By increasing the molar charge ratio, a polyionic solution of the present invention can be "self-cascaded" onto a substrate. In other words, when the substrate is dipped into the solution, alternating layers of polyionic components can be coated onto the substrate. For example, in one embodiment, polyanionic-polycationic-polyanionic alternating repeating layers are assembled when the substrate is dipped into the solution.

Besides containing polyionic components, a polyionic solution of the present invention can also contain various other materials. For example, the polyionic solution can contain antimicrobials, antibacterials, radiation-absorbing materials, cell growth inhibitors, etc.

In accordance with the present invention, it is typically desired to maintain the pH of the solution within a certain range. Maintenance of pH can help prevent precipitation of one of the polyionic components from solution. Accordingly, in one embodiment, the pH is maintained within about ±0.5 of an appropriate pH. Preferably, the pH is maintained within about ±0.1 of an appropriate pH. In general, the appropriate pH for a given solution is at least partially dependent on the polyionic materials selected and can be determined by any suitable method known in the art.

As noted above, after forming the polyionic solution according to the present invention, a substrate material is generally dipped into the solution such that it becomes sufficiently coated. In general, a substrate material of the present invention can be made from any polymeric material. In particular, a substrate material of the present invention can be made from oxygen-permeable polymeric materials. For example, some examples of suitable substrate materials, include, but are not limited to, the polymeric materials disclosed in U.S. Pat. No. 5,760,100 to Nicolson et al., which is incorporated herein by reference.

In some embodiments, the substrate can also be "preconditioned" to enhance the ability of the polyionic solution to coat the substrate. In one embodiment, for example, a layer-by-layer application process can be used to form an underlayer or primer coating on the substrate. This underlayer can sufficiently "roughen" the surface such that the ultimate single-dip coating solution of the present invention can better adhere to the substrate surface.

Moreover, in another embodiment, a solvent solution can be initially applied to the substrate for preconditioning. The application of a solvent, such as an alcohol solution, in the presence of a polyionic component or multiple polyionic components, can allow the substrate to swell. After swelling, the substrate can then be removed from the solvent solution and then dipped into a polyionic solution so that it shrinks. The shrinking of the substrate can entrap the polyionic component(s) within the substrate. As a result, in some embodiments, the ultimate single-dip solution of the present invention more easily adheres to the substrate surface when applied thereto.

In contrast to the heretofore-mentioned layer-by-layer processes, a process of the present invention can apply alternating layers of a polyionic solution to a substrate with only a single dip, thus saving a substantial amount of time. For example, coatings of from about 40 angstroms to about 1000 angstroms can be applied in a single dip. Morever, the time for applying such coating can be less than 6 minutes and even as little as 1 minute.

Other objects, features and aspects of the present invention are discussed in greater detail below.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In general, the present invention is directed to an improved method of coating substrate materials, such as contact lenses, with a solution of negatively and positively charged materials, such as polyionic materials. In particular, the present invention is directed to a process employing a coating solution that includes both a polycation and a polyanion maintained at a certain pH level. It has been discovered that a process of the present invention can sufficiently coat a substrate material with a certain thickness of polyionic layers in a substantially less time period than prior coating processes. For example, in one embodiment, a single dip process of the present invention can be employed to provide a 100 angstrom thick coating in about 6 minutes.

In accordance with the present invention, a coating process is provided that can be utilized to deposit polyionic materials onto a substrate. In one embodiment, for example, a process of the present invention allows the deposition of a bicomponent polyionic solution to a biomaterial substrate, such as a contact lens.

To form a coated substrate of the present invention, a coating solution is initially formed. As stated, a coating solution of the present invention can include polyionic materials, such as polyanionic or polycationic materials. Examples of such polyionic materials are disclosed in U.S. patent application Ser. No. 09/199,609 filed on Nov. 25, 1998, which is incorporated herein by reference and discussed below. For instance, a first material may be a polycationic material, which can include any material known in the art to have a plurality of positively charged groups along a polymer chain. Such materials can include, but are not limited to:

(a) poly(allylamine hydrochloride) (PAH)

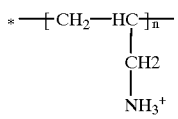

(b) poly(ethyleneimine) (PEI)

(c) poly(vinylbenzyltriamethylamine) (PVBT)

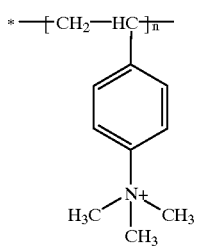

(d) polyaniline (PAN or PANI) (p-type doped) [or sulphonated polyaniline]

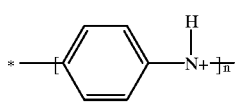

(e) polypyrrole (PPY) (p-typed doped)

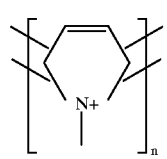

(f) poly(pyridinium acetylene)

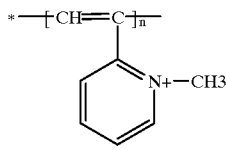

Moreover, a second material may be a polyanionic material, which can generally include any material known in the art to have a plurality of negatively charged groups along a polymer chain. For example, suitable anionic materials can include, but are not limited to:

(a) polymethacrylic acid (PMA)

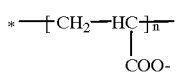

(b) polyacrylic acid (PAA)

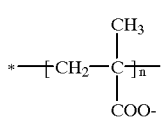

(c) poly(thiophene-3-acetic acid) (PTAA)

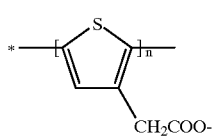

(d) poly(4-styrenesulfonic acid) (PSS) or sodium poly (styrene sulfonate) (SPS) or poly(sodium styrene sulfonate) (PSSS)

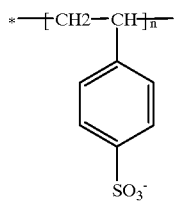

In certain embodiments, either the polyanionic or polycationic material can be made from derivatives of a polyallyl amine having a weight average molecular weight of at least 2000 that, based on the number of amino groups of the polyallyl amine, comprises from approximately 1 to 99% of units having the following formula (1):

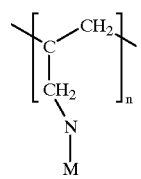

wherein M is a "modifier unit". For instance, in one embodiment, the modifier unit, M, can be R—C=O, where R is $C_2$–$C_6$ alkyl that is substituted by two or more same or different substituents selected from the group consisting of hydroxy, $C_2$–$C_5$ alkanoyloxy, and $C_2$–$C_5$ alkylamino carbonyloxy. Preferably, R is linear $C_3$–$C_6$ alkyl, more preferably linear $C_4$–$C_5$ alkyl, and most preferably n-pentyl that is in each case substituted as defined above.

Suitable substituents of the alkyl radical R are —OH, a radical —O—C(O)—$R_1$, and/or a radical —O—C(O)—NH—$R_1'$, wherein $R_1$ and $R_1'$ are each independently of the other $C_1$–$C_4$ alkyl, preferably methyl, ethyl, iso-, or n-propyl, and more preferably methyl or ethyl. Preferred substituents of the alkyl radical R are hydroxy, acetyloxy, propionyloxy, iso- or n-butanoyloxy, methylaminocarbonyloxy or ethylaminocarbonyloxy, especially hydroxy, acetyloxy, or propionyloxy, and in particular hydroxy.

A particular embodiment of the present invention relates to units of formula (1), wherein R is linear $C_p$-alkyl comprising "p" same or different above-mentioned substituents, and wherein p is 2, 3, 4, 5, or 6, and preferably 4 or 5, and more preferably 5. Alternatively, R may be $C_p$-alkyl comprising "p" hydroxy groups that may be partly or completely acetylated, wherein p is 4 or 5, and preferably 6. Particular radicals R are 1,2,3,4,5-pentahydroxy-n-pentyl or 1,2,3,4,5-pentahydroxy-n-pentyl, wherein the hydroxy groups are partly or completely acetylated.

As stated above, embodiments of a polyionic material of the present invention include derivatives of a polyallyl amine that, based on the number of amino groups of the polyallyl amine, comprise from about 1 to about 99%, in some embodiments from about 10 to about 80%, in some embodiments from about 15 to about 75%, and in other embodiments from about 40 to about 60%, of units of formula (1). In general, polyionic materials of the present invention are also water-soluble.

A particular group of polyallyl amine polymers useful in the present invention comprise at least 1%, in some cases at least 5%, and in other cases at least 10% of units of PAH, based on the number of amino groups of the polyallyl amine. Moreover, one group of polyallyl amine polymers may have a weight average molecular weight of, for example, from 2,000 to 1,000,000, from 3,000 to 500,000, from 5,000 to 150,000, or more particularly from 7,500 to 100,000.

The polyallyl amine polymers described above may be prepared by any manner known in the art. For example, a polyallyl amine having a weight average molecular weight of at least 2,000 that comprises units of PAH may be reacted with a lactone having the following formula (6):

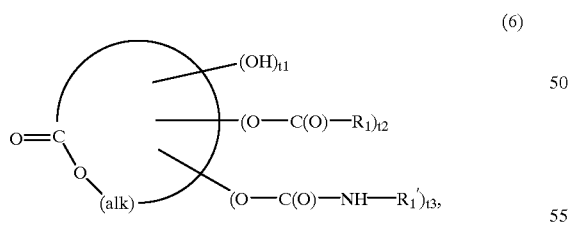
(6)

wherein (alk) is linear or branched $C_2$–$C_6$-alkylene, the sum of (t1-t2-t3) is at least 1, and $R_1$ and $R_1'$ as defined above, to yield a polyallyl amine polymer comprising units of formula (1) and PAH.

The reaction between the polyallyl amine and the lactone may be performed in any manner known in the art, such as, by reacting the polyallyl amine with the lactone in an aqueous medium at a temperature from about 20° C. to about 100° C., and, in some cases, from 30° C. to 60° C. The ratio of units of formula (1) and formula PAH in the final polymer is determined by the stoichiometry of the reactants. The lactones of formula (6) are known or may be prepared according to known methods. Compounds of formula (6), wherein t2 or t3≧1 are, for example, available by reacting the respective hydroxy compound of formula (6) with a compound $R_1$—C(O)X or $R_1'$—NCO under conditions well known in the art. Polyallyl amine starting materials of different molecular weights are commercially available, e.g. in the form of the hydrochloride. Hydrochloride can be converted previously into the free amine, for example, by a treatment with a base, such as sodium or potassium hydroxide solution.

Polyallyl amines comprising additional "modifier units", M, may be prepared by adding to the reaction a mixture of the polyallyl amine and the compound of formula (6), simultaneously or preferably successively. Some examples of compounds that can be added to a polyallyl amine and the compound of formula (6) include, but are not limited to, the following:

(6a)

(6b)

(6c)

(6d)

(6e)

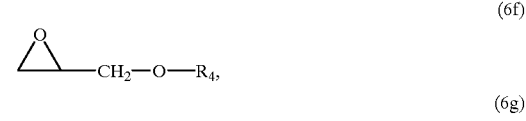
(6f)

(6g)

(6h)

(6i)

(6j)

(6k)

wherein X is halogen, preferably chlorine; (alk') is $C_1$–$C_{12}$-alkylene; $R_{12}$ is hydrogen or $C_1$–$C_2$-alkyl, preferably hydrogen or methyl; and $R_3$, $R_4$, $R_5'$, $R_6$ and $Q_1$ are as defined above. The reaction proceeds, for example, in an aqueous solution at room temperature or at an elevated temperature, such as from 25° C. to about 60° C. and yields various polymers comprising various modifier units.

Because the reaction of the amino groups of the polyallyl amine with the compounds of formulae (6) or (6a)–(6k) proceeds, in general, quantitatively, the structure of the modified polymers is determined mainly by the stoichiometry of the reactants that are employed into the reaction. A particular polyionic material is polyallylamine gluconolactone, as shown below in formula (7):

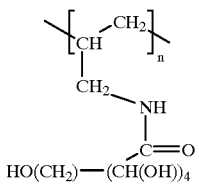

The polyallyl amine may be one in which about 20% to about 80% of the amino groups have been reacted with delta-glucolactone to yield R groups of formula (7).

In order to alter various characteristics of the coating, such as thickness, the molecular weight of the polyionic materials can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 10,000 to about 150,000. In certain embodiments, the molecular weight is about 25,000 to about 100,000, and in other embodiments from about 75,000 to about 100,000.

In addition to polyionic materials, a coating solution of the present invention can also contain additives. As used herein, an additive can generally include any chemical or material. For example, active agents, such as antimicrobials and/or antibacterials can be added to a coating solution of the present invention, particularly when used in biomedical applications. Some antimicrobial polyionic materials include polyquaternary ammonium compounds, such as those described in U.S. Pat. No. 3,931,319 to Green et al. (e.g. POLYQUAD®), which is incorporated herein by reference.

Moreover, others examples of materials that can be added to a coating solution of the present invention are polyionic materials useful for ophthalmic lenses, such as materials having radiation absorbing properties. Such materials can include, for example, visibility tinting agents, iris color modifying dyes, and ultraviolet (UV) light tinting dyes. Still another example of a material that can be added to a coating solution of the present invention is a polyionic material that inhibits or induces cell growth. Cell growth inhibitors can be useful in devices that are exposed to human tissue for an extended time with an ultimate intention to remove (e.g. catheters), while cell growth-inducing polyionic materials can be useful in permanent implant devices (e.g. artificial cornea).

When additives are applied to a coating solution of the present invention, it is generally desired that the additives have some charge. By having a positive or negative charge, the additive can be substituted for one of the polyionic materials in solution at the same molar charge ratio. For example, polyquaternary ammonium compounds typically have a positive charge. As such, these compounds can be substituted into a solution of the present invention for the polycationic component such that the additive is applied to a substrate material in a manner similar to how a polycationic would be applied.

It should be understood, however, that non-charged additives can also be applied to a substrate material of the present invention. For example, in one embodiment, a polycationic layer can be first applied onto a substrate material. Thereafter, a non-charged additive can be applied and immediately entrapped by a polyanionic material applied thereon. In this embodiment, polyanionic material can sufficiently entrap the non-charged additive between two layers of polyionic material. After such entrapment, the substrate material can then be coated with other layers of polyionic materials in accordance with the present invention.

As discussed above, a coating solution of the present invention can generally be formed from polyionic materials and various other chemicals. In one embodiment, a coating solution of the present invention can be a bicomponent solution that contains at least one polycationic and polyionic material. In other embodiments, the coating solution can contain more than two components of a polyionic materials, such as 3, 4, or 5 components.

Regardless of the number of polyionic components present within a coating solution of the present invention, it is typically desired that one of the polyionic components of the solution be present in a greater amount than another component such that a non-stoichiometric solution can be formed. For example, when a polyanionic/polycationic bicomponent solution is formed, either one of the polyionic components can be present in an amount greater than the other component. By forming a solution from polyionic materials in such a manner, a substrate material can be suitably coated with the coating solution in a single dip. Specifically, the non-stoichiometric concentrations of polyionic materials provides a solution that can "self-cascade" such that alternating layers of polyionic materials are formed onto the substrate with a single dip.

To control the amount of each polyionic component within a coating solution, the "molar charge ratio" can be varied. As used herein, "molar charge ratio" is defined as the ratio of charged molecules in solution on a molar basis. For example, a 10:1 molar charge ratio can be defined as 10 molecules of a polyanion to 1 molecule of a polycation, or 10 molecules of a polycation to 1 molecule of a polyanion. The molar charge ratio can be determined as defined above for any number of components within a solution, as long as at least one polycation and one polyanion are included therein.

As the molar charge ratio is substantially increased, the structure of the coating on a particular substrate can become more "open". In some instances, such an opening of the coating structure can result in the requirement of more dipping steps to achieve the desired coating on the substrate material. In this regard, a coating solution of the present invention typically has a "molar charge ratio" from about 3:1 to about 100:1. In one embodiment, the coating solution has a molar charge ratio of about 5:1 (polyanion:polycation). In another embodiment, the coating solution has a molar charge ratio of about 1:5 (polyanion:polycation). In still another embodiment, a 3:1 or 1:3 molar charge ratio may be utilized.

In a certain embodiment, the coating solution has a molar charge ratio of about 10:1 (polyanion:polycation). By employing a coating solution having a predominant amount of polyanionic material, a substrate material can be coated in a manner such that the outer layer is a polyanionic material. Substrates having an outer polyanionic material are typically more acidic. It is believed that in some applications, an acidic outer layer can provide a more hydrophilic substrate and allow better wetting. However, it should be understood that an outer layer of polycationic material may also be desirable. In contrast to a polyanionic outer coating, a polycationic outer coating can be achieved by providing a coating solution that contains a predominant amount of polycationic material.

In accordance with the present invention, a coating solution of the present invention is typically maintained at a certain pH level such that the solution remains stable. When the pH of the coating solution is improperly varied, a salt can sometimes form through back-titration. Such precipitation can often have an adverse affect on the ability of the coating solution to coat the substrate layer as desired. As such, depending on the particular coating solution used, the pH of the solution is normally maintained at a value within about ±0.5 of the appropriate pH range for the solution. In certain embodiments, the pH of the coating solution is maintained at a pH of ±0.1 of the appropriate pH range for the solution. By maintaining the pH of the solution within a specified range of the appropriate pH for the solution, precipitation can be substantially inhibited.

The appropriate pH range for a coating solution can vary depending on the particular polyionic materials chosen. Any suitable method known in the art can be utilized to determine the appropriate pH range for a given solution. One such method is described in "Controlling Bilayer Composition and Surface Wettability of Sequentially Adsorbed Multilayers of Weak Polyelectrolytes" by Dougsik Yoo, Seimel S. Shiratori, and Michael R. Rubner, which is published in MACROMOLECULES® Volume 31, Number 13, pages 4309–4318 (1998). For example, in a particular embodiment, a 10:1 (polyanion:polycation) ratio of polyacrylic acid and polyallylamine hydrochloride is utilized. For this particular bicomponent coating solution, the appropriate pH range was determined to be about 2.5.

In accordance with the present invention, a coating solution of the present invention, as described above, can be prepared in a variety of ways. In particular, a coating solution of the present invention can be formed by dissolving the polyionic materials in water or any other material that sufficiently dissolves the material. When a solvent is used, any solvent that can allow the components within the coating solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of the polyionic materials within a coating solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.001% to about 0.25% by weight, between about 0.005% to about 0.10% by weight, or between about 0.01% to about 0.05% by weight.

In this regard, one embodiment a bicomponent coating solution of the present invention can be prepared as follows. However, it should be understood that the following description is for exemplary purposes only and that a coating solution of the present invention can be prepared by other suitable methods.

A bicomponent coating solution can be prepared by first dissolving a single component polyanionic material in water or other solvent at a designated concentration. For example, in one embodiment, a solution of polyacrylic acid having a molecular weight of about 90,000 is prepared by dissolving a suitable amount of the material in water to form a 0.001M PAA solution. Once dissolved, the pH of the polyanionic solution can be properly adjusted by adding a basic or acid material. In the embodiment above, for example, a suitable amount of 1N hydrochloric acid (HCl) can be added to adjust the pH to 2.5.

After preparing the polyanionic solution, the polycationic solution can be similarly formed. For example, in one embodiment, poly(allylamine hydrochloride) having a molecular weight of about 50,000 to about 65,000 can be dissolved in water to form a 0.001M solution. Thereafter, the pH can be similarly adjusted to 2.5 by adding a suitable amount of hydrochloric acid.

The formed solutions can then be mixed to form a single-dip coating solution of the present invention. In one embodiment, for example, the solutions above can be mixed slowly to form the coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

Once a coating solution is formed in accordance with the present invention, it can then be applied to a substrate material. In one embodiment, a coating solution of the present invention can also be applied to a mold for forming a polymeric material, such as disclosed in co-pending U.S. patent application entitled "Method for Modifying a Surface" (filed on the same day as present application), which is incorporated herein by reference. Thus, although the embodiment discussed below relates to the direct application of a coating solution to the substrate material, other methods of coating the substrate are equally suitable.

Thus, to coat a substrate material, it can be dipped into a coating solution such that the substrate becomes sufficiently coated with the polyionic materials. The coating solution contains both a polyanion and polycation within a single solvent such that a single dip can result in alternating layers of polyionic material. For example, a single dip of a substrate material can result in the substrate being coated with cascaded layers of polyanion-polycation-polyanion-polycation, etc.

In general, a substrate material dipped into a coating solution can be made from any polymeric material, such as contact lenses, molds for forming contact lenses, or shaped polymeric materials. When forming a contact lens, the substrate material may be an oxygen-permeable material, such as flourine- or siloxane- containing polymers. For example, the polymeric materials described in U.S. Pat. No. 5,760,100 to Nicolson et al., are suitable substrate materials for use in the present invention. For illustrative purposes, other examples of suitable materials are disclosed below, without limitation.

One embodiment of a suitable substrate material of the present invention is a copolymer formed from the following monomeric and macromeric components:

(a) about 5 to about 94 dry weight percent of a macromer having the segment of the formula:

CP-PAO-DU-ALK-PDMS-ALK-DU-PAO-CP where

PDMS is a divalent poly(disubstituted siloxane),

ALK is an alkylene or alkylenoxy group having at least 3 carbon atoms,

DU is a diurethane-containing group,

PAO is a divalent polyoxyalkylene, and

CP is selected from acrylates and methacrylates, wherein said macromer has a number-average molecular weight of about 2000 to about 10,000;

(b) about 5 to about 60 weight percent methacryloxypropyltris (trimethylsiloxy)silane;

(c) about 1 to about 30 weight percent of an acrylate or methacrylate monomer; and (d) 0 to about 5 weight percent cross-linking agent, with the weight percentages being based upon the dry weight of the polymer components.

Moreover, a particular polysiloxane macromer segment is defined by the formula:

CP-PAO-DU-ALK-PDMS-ALK-DU-PAO-CP where
PDMS is a divalent poly(disubstituted siloxane);
CP is an isocyanatoalkyl acrylate or methacrylate, preferably isocyanatoethyl methacrylate, where the urethane group is bonded to the terminal carbon on the PAO group;
PAO is a divalent polyoxyalkylene (which may be substituted), and is preferably a polyethylene oxide, i.e., $(-CH_2-CH_2-O-)_m CH_2-CH_2-$ where m may range from about 3 to about 44, more preferably about 4 to about 24;
DU is a diurethane (which may be a cyclic structure), where an oxygen of the first urethane linkage is bonded to the PAO group and an oxygen of the second urethane linkage is bonded to the ALK group;
and ALK is an alkylene or alkylenoxy group having at least 3 carbon atoms, such as a branched alkylene group or an alkylenoxy group having 3 to 6 carbon atoms, such as a sec-butyl (i.e., $-CH_2CH_2CH(CH_3)-$) group or an ethoxypropoxy group (e.g., $-O-(CH_2)_2-O-(CH_2)_3-$).

Another embodiment of a suitable substrate material of the present invention is a macromer having the following general formula I:

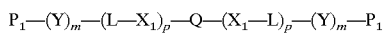

where each $P_1$, independently of the others, is a free radical-polymerizable group;
each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—;
m and p, independently of one another, are 0 or 1;
each L, independently of the others, is a divalent radical of an organic compound having up to 20 carbon atoms;
each $X_1$, independently of the others, is —NHCO—, —CONH—, —NHCONH—, —COO—, —OCO—, —NHCOO— or —OCONH—; and
Q is a bivalent polymer fragment consisting of the segments:
(a) $-(E)_k-Z-CF_2-(OCF_2)_x-(OCF_2CF_2)_y-OCF_2-Z-(E)_k-$,
where x+y is a number in the range of about 10 to about 30;
each Z, independently of the others, is a divalent radical having up to about 12 carbon atoms or Z is a bond;
each E, independently of the others, is $-(OCH_2CH_2)_q-$, where q has a value of from 0 to about 2, and where the link —Z—E—represents the sequence $-Z-(OCH_2CH_2)_q-$; and k is 0 or 1;

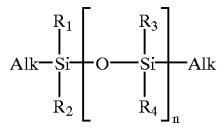

where n is an integer from about 5 to about 100;
Alk is alkylene having up to about 20 carbon atoms;
about 80% to about 100% of the radicals $R_1$, $R_2$, $R_3$ and $R_4$, independently of one another, are alkyl and 0 to about 20% of the radicals $R_1$, $R_2$, $R_3$ and $R_4$, independently of one another, are alkenyl, aryl or cyanolkyl; and
(c) $X_2-R-X_2$,
where R is a divalent organic radical having up to 20 carbon atoms; and
each $X_2$, independently of the others, is —NHCO—, —CONH—, —NHCONH—, —COO—, —OCO—, —NHCOO—, or OCONH—;
with the provisos that there is typically at least one of each segment (a), (b), and (c) in Q, that each segment (a) or (b) has a segment (c) attached to it, and that each segment (c) has a segment (a) or (b) attached to it.

The number of segments (b) in the polymer fragment may be greater than or equal to the number of segments (a). The ratio between the number of segment (a) and (b) in the polymer fragment Q, for example, may be about 3:4, 2:3, 1:2 or 1:1. The molar ratio between the number of segments (a) and (b) in the polymer fragment Q may be, for example, 2:3, 1:2 or 1:1.

The mean molecular weight of the polymer fragment Q is in the range of about 1,000 to about 20,000, sometimes in the range of about 3000 to about 15,000, and sometimes in the range of about 5,000 to about 12,000.

The total number of segments (a) and (b) in the polymer fragment Q may be in the range of about 2 to about 11, in the range of about 2 to about 9, or in the range of about 2 to about 7. The smallest polymer unit Q may be composed of one perfluoro segment (a), one siloxane segment (b) and one segment (c).

In still another embodiment of the present invention, the substrate material can be formed by polymerizing macromers that contain free hydroxyl groups. Macromers that are built up, for example, from an amino-alkylated polysiloxane derivatized with at least one polyol component that contains an unsaturated polymerizable side chain may be utilized. In one embodiment, polymers can be prepared from the macromers according to the invention by homopolymerization. The macromers mentioned can also be mixed and polymerized with one or more hydrophilic and/or hydrophobic comonomers. A special property of the macromers according to the invention is that they function as the element which controls microphase separation between selected hydrophilic and hydrophobic components in a cross-linked end product. The hydrophilic/hydrophobic microphase separation is in the region of less than about 300 nm. The macromers may be cross-linked at the phase boundaries between, for example, an acrylate comonomer on the one hand and an unsaturated polymerizable side chain of polyols bonded to polysiloxane by covalent bonds, and additionally by reversible physical interactions such as hydrogen bridges. These are formed, for example, by numerous amide or urethane groups. The continuous siloxane phase that exists in the phase composite has the effect of producing a high permeability to oxygen.

The polymers of this embodiment can be formed by polymerizing a macromer comprising at least one segment having the following general formula (II):

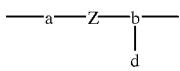

in which,
(a) is a polysiloxane segment,
(b) is a polyol segment which contains at least 4 carbon atoms,
Z is a segment (c) or a group X1, and
(c) is defined as $X_2$—R—$X_2$, wherein
  R is a bivalent radical of an organic compound having up to 20 carbon atoms and
  each $X_2$ independently of the other is a bivalent radical which contains at least one carbonyl group,
$X_1$ is defined as $X_2$, and
(d) is a radical having the following general formula (III):

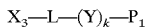

in which,
$P_1$ is a group that can be polymerized by free radicals;
Y and $X_3$ independently of one another are a bivalent radical which contains at least one carbonyl group;
k is 0 or 1; and
L is a bond or a divalent radical having up to 20 carbon atoms of an organic compound.

In one embodiment, a polysiloxane segment (a) can be derived from a compound having the following general formula (IV):

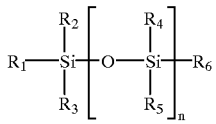

in which,
n is an integer from 5 to 500;
25%–99.8% of the radicals $R_1$, $R_2$, $R_3$, $R_4$, $R_5$, and $R_6$ independently of one another are alkyl and 0.2%–75% of the radicals $R_1$, $R_2$, $R_3$, $R_4$, $R_5$, and $R_6$ independently of one another are partly fluorinated alkyl, aminoalkyl, alkenyl, aryl, cyanoalkyl, alk—NH—alk—$NH_2$ or alk—$(OCH_2)_m$—$(OCH_2)_p$—$OR_7$,
where $R_7$ is hydrogen or lower alkyl, alk is alkylene, and
m and p independently of one another are an integer from 0 to 10, one molecule containing at least one primary amino or hydroxyl group.

The alkylenoxy groups —$(OCH_2CH_2)_m$ and —$(OCH_2)_p$ in the siloxane of the formula (IV) are either distributed randomly in a ligand alk—$(OCH_2CH_2)_m$—$(OCH2)p$—$OR_7$ or are distributed as blocks in a chain.

A polysiloxane segment (a) is linked a total of about 1 to about 50 times, and, for example, about 2 to about 30 times, and in particular about 4 to about 10 times, via a group Z with a segment (b) or another segment (a), Z in an a-Z-a sequence typically being a segment (c). The linkage site in a segment (a) with a group Z is an amino or hydroxyl group reduced by one hydrogen.

Another embodiment of a substrate material of the present invention involves the polymerization of a siloxane-containing macromer formed from a poly(dialkylsiloxane) dialkoxyalkanol having the following structure (V):

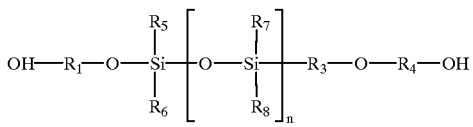

where n is an integer from about 5 to about 500, preferably about 20 to about 200, more preferably about 20 to about 100;
the radicals $R_1$, $R_2$, $R_3$, and $R_4$, independently of one another, are lower alkylene, for example a $C_1$-$C_6$ alkylene, $C_1$-$C_3$ alkylene, and wherein, in some embodiments, the total number of carbon atoms in $R_1$ and $R_2$ or in $R_3$ and $R_4$ is greater than 4; and
$R_5$, $R_6$, $R_7$, and $R_8$ are, independently of one another, lower alkyl, in some embodiments, a $C_1$-$C_6$ alkyl, and in some embodiments, a $C_1$-$C_3$ alkyl.

The general structure of the macromer discussed above is as follows:

ACRYLATE-LINK-ALK-O-ALK-PDAS-ALK-O-ALK-LINK-ACRYLATE where the ACRYLATE is selected from acrylates and methacrylates; LINK is selected from urethanes and diurethane linkages, ALK-O-ALK is, as defined above, ($R_1$—O—$R_2$ or $R_3$—O—$R_4$), and PDAS is a poly(dialkylsiloxane).

For example, the macromer described above can be prepared by reacting isophorone diisocyanate, 2-hydroxyethyl (meth)acrylate and a poly(dialkylsiloxane) dialkoxyalkanol in the presence of a catalyst.

In some embodiments of the present invention, the particular substrate material utilized can also be "preconditioned" or "oriented" before being dipped into a coating solution. Although not required, pre-conditioning the substrate material in accordance with the present invention can enhance the "self cascading" of polyionic layers in a single dip process. In particular, pre-conditioning a substrate material typically involves increasing the roughness of the substrate surface.

In this regard, the roughness of the substrate surface can be altered in a variety of ways. Generally, an "underlayer" or "primer layer" of coating solution can be initially applied to the substrate material to accomplish the desired surface alteration. For example, in one embodiment, one or more standard layer-by-layer dip coatings can be employed as an underlayer for the ultimate dip coating of the present invention. The "underlayer" can be applied by any method known in the art, such as by spray-coating, dipping, etc. Examples of such methods are disclosed in detail in co-pending U.S. application Ser. No. 09/199,609. In some embodiments, the underlayer can be made from a polyionic material, such as poly(ethyleneimine). After applying this primer coating or underlayer, in one embodiment, the substrate can then be dipped into the ultimate coating solution. For instance, in one embodiment, the ultimate coating solution can contain poly(allylamine hydrochloride) and polyacrylic acid. In still another embodiment, the coating solution can contain poly (allylamine hydrochloride) and sodium poly(styrene sulfonate).

Moreover, in another embodiment, the substrate material can be allowed to swell in a solvent solution containing a solvent and at least one polyionic component(s). In general, any solvent that can allow the components within the coating solution to remain stable in water is suitable for use in the present invention. Examples of suitable alcohols can include, but are not limited to, isopropyl alcohol, hexanol, ethanol, etc. In certain embodiments, the substrate material is first allowed to swell in an alcohol solution containing about 20% isopropyl alcohol and about 80% water. In some embodiments, the alcohol solution used to swell the substrate can also be used as the solvent in the ultimate single-dip polyionic coating solution.

After swelling, the substrate material can then be removed from the solvent solution and allowed to "shrink". This "shrinking" step causes the substrate material to entrap the initial layer of the polycation or polyanion present within the solvent solution. The swelling/entrapment process described in this embodiment can enhance the ability of the coating solution to coat the substrate material.

It has been discovered that, in most cases, a process of the present invention can apply a coating solution to a substrate material with only a single dip. As such, in contrast to the aforementioned LbL process, a process of the present invention can apply a coating in relatively little time. For example, coatings can be applied in a time period as little as one minute. Moreover, in some applications, a 100 angstrom coating can be applied in about 6 minutes using a single dip, whereas a similar coating could take approximately 10 hours to apply using the aforementioned LbL process (e.g. 20 dips). Moreover, it has been discovered that, in certain applications, a process of the present invention can apply coatings from about 40 angstroms to about 2000 angstroms in a single dip.

However, it may often be desired to apply a coating having a substantial thickness that cannot be sufficiently applied with a single dip. For example, in one embodiment of the present invention, a 500 angstrom coating is applied to a substrate material in two dipping steps. In particular, a 10:1 polyanion to polycation dip is first applied to the substrate material. Thereafter, a 1:10 polyanion to polycation is employed as a second coating layer. In some embodiments, more than two dips, such as 3 to 5 dips in multi-component solutions of the present invention can be utilized. For example, when coating a contact lens material according to the present invention, three dips may be utilized. However, even when more than one dipping step is utilized with solutions of the present invention, the substrate material can still be coated in substantially less time than with a LbL process. In fact, a LbL process could take approximately 50 hours (e.g. 100 dips) to apply a 500 angstrom coating, while a process of the present inventive single dip process can take approximately 8 to 30 minutes (e.g. 4 or 5 dips) to achieve the same thickness.

In one embodiment of the present invention, the single-dip solution can also be utilized for coating of a mold used to define the shape of an article. Coating a mold in this manner can prove useful in processes such as transfer grafting a polyionic coating. An example of such a process is disclosed in more detail with a co-pending U.S. Patent Application entitled "Method of Modifying a Surface" (filed on the same day as the present application). In one embodiment, the mold is coated with a polyionic solution of the present invention, but at least a portion of the coating is transferred from the mold when the liquid molding material (e.g., polymerizable material) is dispensed into the mold for formation of the solid article. Hence, another embodiment of the invention is a method of forming an article and coating the article by transfer grafting a coating material from the mold in which the article was produced. This method includes the steps of applying a coating of a polyionic solution to a mold by contacting at least a portion of the mold with the solution, dispensing a liquid molding material into the mold, thereby contacting said liquid molding material with said coating, allowing the mold coating to contact the liquid molding material during curing and causing the liquid mold material to harden (e.g., by polymerization via application of UV light). As a result, the coating can remain in tact and "transfer" to the solidified article.

The present invention may be better understood by reference to the following examples. In particular, Examples 1–3 illustrate a standard layer-by-layer process, while Examples 5–8 illustrate a single-dip process of the present invention.

EXAMPLE 1

The ability of polyionic materials to be coated onto a contact lens using layer-by-layer dipping was demonstrated. The substrate material (i.e. contact lens) was prepared with materials such as described in U.S. Pat. No. 5,760,100 to Nicolson et al.

A sample contact lens was initially coated with a primer layer by dipping the lens into a PEI solution for 5 minutes. The PEI solution was prepared by dissolving PEI powder in water such that a 0.001M PEI solution resulted. After dipping, the lens was rinsed for 2 minutes in consecutive rinse baths. Once the above steps were completed, the lens was then dipped into a PAA solution for 5 minutes, rinsed for 2 minutes, rinsed for 2 minutes, dipped into a PAH solution for 5 minutes, rinsed for 2 minutes, rinsed for 2 minutes, dipped into a PAA solution for 5 minutes, etc., until 10 bilayers of polyionic material were formed onto the lens. The PAA and PAH solutions were prepared by dissolving the respective powders in water to form 0.001M solutions. It was determined that 20 dipping steps, taking 180 minutes, were required to form a 100 to 200 angstrom coating.

EXAMPLE 2

The ability of polyionic materials to be coated onto a contact lens using layer-by-layer dipping and air drying was demonstrated. The substrate material (i.e. contact lens) was prepared with materials, such as described in U.S. Pat. No. 5,760,100 to Nicolson et al.

A sample contact lens was initially coated with a primer layer by dipping the lens into a PEI solution for 5 minutes. The PEI solution was prepared by as described in Example 1. After dipping, the lens was dried for 1 minute with an air knife. Once the above steps were completed, the lens was then dipped into a PM solution for 5 minutes, dried with an air knife for 1 minute, dipped into a PAH solution for 5 minutes, dried for 1 minute, dipped into a PM solution for 5 minutes, etc., until 10 bilayers of polyionic material were formed onto the lens. The PM and PAH solutions were prepared as described in Example 1.

It was determined that 20 dipping steps, taking 120 minutes, were required to form a 100 to 200 angstrom coating.

EXAMPLE 3

The ability of polyionic materials to be coated onto a contact lens using layer-by-layer spraying and air drying was demonstrated. The substrate material (i.e. contact lens) was prepared with materials, such as described in U.S. Pat. No. 5,760,100 to Nicolson et al.

A sample contact lens was initially coated with a primer layer by spraying a PEI solution onto the lens for 1 minute using an ultrasonic nozzle. The PEI solution was prepared as described in Example 1. After spraying, the lens was dried for 1 minute with an air knife. Once the above steps were completed, the lens was again sprayed with a PM solution for 1 minute, dried for 1 minute, sprayed with a PAH solution for 1 minute, dried for 1 minute, sprayed with a PM solution for 1 minute, etc., until 10 bilayers of polyionic material were formed onto the lens. The PAA and PAH solutions were prepared as described in Example 1.

It was determined that 20 spray steps, taking 40 minutes, were required to form a 200 to 300 angstrom coating.

EXAMPLE 4

The ability of polyionic materials to be coated onto a contact lens in a relatively short amount of time using a solution of the present invention was demonstrated. The substrate material (i.e. contact lens) was prepared with materials, such as described in U.S. Pat. No. 5,760,100 to Nicolson et al.

A sample contact lens was coated using single dip solutions of the present invention. In particular, the lens was coated as follows. Initially, a primer layer was applied to the lens by spraying a PEI solution onto the lens for 1 minute (using an ultrasonic nozzle), drying the lens for 1 minute (using an air knife), spraying with a PAA solution for 1 minute, drying for 1 minute, spraying with a PEI solution for 1 minute, drying for 1 minute, spraying with a PAA solution for 1 minute, and drying for 1 minute. The PEI and PAA solutions were prepared as described in Example 1. After applying the primer coating, the lens was dipped in a predominantly polyanionic single-dip solution for 1 minute, dried for 1 minute, dipped into a predominantly polycationic single-dip solution for 1 minute, and dried for 1 minute such that a 10 bilayer coating was formed. The single-dip solutions used above were formed as follows. A solution of polyacrylic acid having a molecular weight of about 90,000 was prepared by dissolving a suitable amount of the material in water to form a 0.001M PAA solution. Once dissolved, the pH of the polyanionic solution was adjusted by adding 1N hydrochloric acid until the pH reached 2.5. After preparing the above solution, poly(allylamine hydrochloride) having a molecular weight of about 50,000 to about 65,000 was dissolved in water to form a 0.001M solution. Thereafter, the pH was similarly adjusted by adding hydrochloric acid until a pH of 2.5 was obtained.

A portion of the solutions were then mixed to form the predominantly polyanionic single-dip coating solution. Specifically, a single-dip solution having a 10:1 molar charge ratio (polyanion:polycation) was formed by adding 1 part (by volume) of the PAH solution into 10 parts (by volume) of the PAA solution. The predominantly polycationic single-dip solution was similarly formed into a solution having a 1:10 molar charge ratio (polyanion:polycation) by adding 1 part (by volume) of the PAA solution into 10 parts (by volume) of the PAH solution.

It was determined that only 4 spray steps (primer layer) and 2 dips, taking only 12 minutes, were needed to form about a 1 micron coating on the lens. As can be seen from the results of the example, a single-dip solution of the present invention can allow the coating of substrate materials in faster times than standard layer by layer processes.

EXAMPLE 5

The ability of polyionic materials to be first coated onto a mold so that a contact lens can be formed within the mold and the coating can transfer from the mold to the contact lens was demonstrated. The substrate material (i.e. contact lens) was prepared with materials, such as described in U.S. Pat. No. 5,760,100 to Nicolson et al. and the molds were made by cast molding techniques, such as described herein.

A sample mold was initially coated with a primer layer by spraying a PAA solution onto the lens for 1.5 seconds using an ultrasonic nozzle. The PAA solution was prepared as described in Example 1. After spraying, the mold was sprayed with water for 3 seconds. Thereafter, the mold was sprayed with a PEI solution for 1.5 seconds followed with water for 3 seconds. The PEI solution was prepared as described in Example 1. The mold was again sprayed with the PAA solution for 1.5 seconds and water for 3 seconds. A PAH solution was then sprayed onto the mold for 1.5 seconds, followed by a water spray for 3 seconds. The PAH solution was prepared as described in Example 1. Once the above steps were completed, the mold was again sprayed with a PAA solution for 1 minute, sprayed with water for 3 seconds, sprayed with a PAH solution for 1.5 seconds, sprayed with water for 3 seconds, sprayed with a PAA solution for 1.5 seconds, sprayed with water for 3 seconds, sprayed with a PAH solution for 1.5 seconds, sprayed with water for 3 seconds, sprayed with a PAA solution for 1.5 seconds, sprayed with water for 3 seconds, sprayed with PAH for 1.5 seconds, sprayed with water for 3 seconds, etc., until 5 bilayers of polyionic material were formed onto the mold.

Once the molds were coated, a polymeric substrate material, such as disclosed herein, was then dispensed into the mold. Thereafter, the polymeric substrate material was cast, cured, and extracted through isopropyl alcohol extraction as is well known in the art. After being removed, the sample lens was dipped into a predominantly polyanionic single-dip solution for 2 to 5 minutes.

The single-dip solution used above was formed as follows. A solution of polyacrylic acid having a molecular weight of about 90,000 was prepared by dissolving a suitable amount of the material in water to form a 0.001M PAA solution. Once dissolved, the pH of the polyanionic solution was adjusted by adding 1N hydrochloric acid until the pH reached 2.5. After preparing the above solution, poly(allylamine hydrochloride) having a molecular weight of about 50,000 to about 65,000 was dissolved in water to form a 0.001M solution. Thereafter, the pH was similarly adjusted by adding hydrochloric acid until a pH of 2.5 was obtained. A portion of the solutions were then mixed to form the predominantly polyanionic single-dip coating solution. Specifically, a single-dip solution having a 10:1 molar charge ratio (polyanion:polycation) was formed by adding 1 part (by volume) of the PAH solution into 10 parts (by volume) of the PAA solution.

It was determined that a 5 bilayer coating was achieved with a spray time of 1.5 minutes and a dip time of 2 to 5 minutes to form a 200 to 400 angstrom coating. Moreover, it was also determined that essentially the entire coating transferred to the solidified article.

EXAMPLE 6

The ability of polyionic materials to be transferred from a mold to a contact lens formed within the mold was demonstrated. The substrate material (i.e. contact lens) was prepared with materials, such as described in U.S. Pat. No. 5,760,100 to Nicolson et al. and the molds were made by cast molding techniques, such as described herein.

A sample mold was initially coated with a primer layer by spraying a PAA solution onto the lens for 1.5 seconds using an ultrasonic nozzle. The PAA solution was prepared as described in Example 1. After spraying, the mold was sprayed with water for 3 seconds. Thereafter, the mold was sprayed with a PEI solution for 1.5 seconds followed with water for 3 seconds. The PEI solution was prepared as described in Example 1. The mold was again sprayed with the PAA solution for 1.5 seconds and water for 3 seconds. A PAH solution was then sprayed onto the mold for 1.5 seconds, followed by a water spray for 3 seconds. The PAH solution was prepared by as described in Example 1.

Once the above steps were completed, the mold was dipped into a predominantly polyanionic single-dip solution for 5 minutes, rinsed with water for 1 minute, dipped into a predominantly polycationic single dip solution for 1 minute, and rinsed with water for 1 minute. After applying the coating to the mold, a polymeric substrate material was dispensed into the mold, cured, and extracted as described in Example 5. Thereafter, the finished contact lens was dipped into a predominantly polyanionic single dip solution for 2 to 5 minutes.

The single-dip solutions used above were formed as follows. A solution of polyacrylic acid having a molecular weight of about 90,000 was prepared by dissolving a suitable amount of the material in water to form a 0.001M PAA solution. Once dissolved, the pH of the polyanionic solution was adjusted by adding 1N hydrochloric acid until the pH reached 2.5. After preparing the above solution, poly (allylamine hydrochloride) having a molecular weight of about 50,000 to about 65,000 was dissolved in water to form a 0.001M solution. Thereafter, the pH was similarly adjusted by adding hydrochloric acid until a pH of 2.5 was obtained.

Portions of the solutions were then mixed to form the predominantly polyanionic single-dip coating solution. Specifically, a single-dip solution having a 10:1 molar charge ratio (polyanion:polycation) was formed by adding 1 part (by volume) of the PAH solution into 10 parts (by volume) of the PAA solution. The predominantly polycationic single-dip solution was similarly formed into a solution having a 1:10 molar charge ratio (polyanion:polycation) by adding 1 part (by volume) of the PAA solution into 10 parts (by volume) of the PAH solution.

It was determined that a 5 bilayer coating having a thickness of approximately 1 micron could be formed in 13 minutes for each lens.

EXAMPLE 7

A contact lens was coated by just one dip using an embodiment of the single dip solution described herein. In particular, the lens was coated after it was allowed to swell in isopropyl alcohol (IPA). After 2 to 5 minute soak, the lenses were removed from the alcohol solution and then dipped for approximately 5 min into a 0.001M solution containing both polyacrylic acid having a molecular weight of about 90,000 and poly(allylamine hydrochloride) having a molecular weight of about 60,000 at a 10:1 molar charge ratio (polyanion/polycation) and a pH of 2.5. After dipping, the lenses were placed in phosphate buffered saline and autoclaved (sterilized).

The single-dip solution employed in this Example 7 was prepared as follows: A solution of polyacrylic acid having a molecular weight of about 90,000 was prepared by dissolving a suitable amount of the material in water to form a 0.001M PAA solution. Once dissolved, the pH of the polyanionic PAA solution was adjusted by adding 1N hydrochloric acid until the pH reached 2.5. Then, a solution of poly(allylamine hydrochloride) having a molecular weight of about 60,000 was prepared by dissolving a suitable amount of the material in water to form a 0.001M PAH solution. Thereafter, the pH of the polycationic PAH solution was similarly adjusted by adding 1N hydrochloric acid until a pH of 2.5 was obtained.

A portion of the PAA and PAH solutions were then mixed to form the predominantly polyanionic single-dip coating solution. Specifically, a solution having a 10:1 molar charge ratio (polyanion/polycation) was formed by adding 1 part (by volume) of the PAH solution into 10 parts (by volume) of the PAA solution.

It was determined that a hydrophilic coating on a contact lens with a contact angle of 50° or less could be achieved by just one 5 minute or less dip in a single-dip solution of the present invention.

EXAMPLE 8

The ability of polyionic materials to be deposited onto a contact lens mold was demonstrated. Various contact lenses were coated using three coating methods. For each lot below, the substrate material (i.e. contact lens) was prepared with materials, such as described in U.S. Pat. No. 5,760,100 to Nicolson et al. and the molds were made by cast molding techniques, such as described herein.

Dip coated lenses (Lot #1): The first lot of contact lenses was prepared by dipping the lenses into the polyionic materials. Initially, the contact lenses were swelled in an isopropyl alcohol solution. After sufficient swelling, the lenses were then dipped into a 0.001M solution (Solution A) that contained poly(allylamine hydrochloride) having a MW of about 60,000 and polyacrylic acid having a MW of about 90,000 at a 10:1 molar charge ratio (polyanion/polycation) and a pH of 2.5. The lenses remained in the solution for 5 minutes and were thereafter rinsed with water for approximately 1 minute. After dipping the lenses into Solution A and rinsing, the lenses were dipped into a second 0.001M solution (Solution B) that contained the same polyionic materials and pH, but having a molar charge ratio of 1:10 (polyanion/polycation). The lenses remained in this solution for 5 minutes. After dipping, the lenses were rinsed for about 1 minute with water.

Spray coated molds (Lot #2): The second lot of contact lenses was prepared by spraying molds with polyionic materials prior to forming the lenses. The molds were sprayed with a 0.001M solution that contained poly (ethyleneimine) for about 1 minute using an ultrasonic nozzle. Thereafter, the lenses were rinsed and sprayed with a 0.001M solution of polyacrylic acid for about 1 minute. These steps were repeated into 3 bilayers were formed onto the mold. After applying the sprayed coating, the lens materials were dispensed into the molds and cured. The lenses were then extracted with isopropyl alcohol.

Dip coated molds (Lot #3): The third lot of contact lenses was prepared by dipping the sprayed molds above into other solutions of polyionic materials. After being sprayed, the molds were dipped into Solution A for about 5 minutes, rinsed in water for about 1 minute, dipped into Solution B for about 5 minutes, and rinsed again in water for about 1 minute. After dipping, the lens materials were dispensed into the molds and cured. The lenses were then extracted with isopropyl alcohol, dipped into Solution A for about 5 minutes, and then dipped into Solution B for about 5 minutes.

Control: For each lot of lenses made according to the three sets of conditions given above, a plasma treated lens was also prepared as a control. One such technique for forming a plasma treated lens is described in PCT Publication No. WO 96/31792 to Nicolson et al.

After the lenses were prepared, they were tested on 30 subjects by placing one of the lenses from Lots 1, 2, or 3 in one eye for 6 hours and placing a plasma coated lens (control) in the other eye for 6 hours. After the 6-hour period, the results shown in Table 1 were obtained.

TABLE 1

Comparison of Surface Properties of the Lenses

| Lot | IP | DK | Contact Angle | NISDT (sec) (Plasma Control) | Comfort (Plasma Control) |
|---|---|---|---|---|---|
| 1 | 1.27 | 112 | 61 | 6.7(8.0) | 78(72) |
| 2 | 1.41 | 94 | 74 | 5.9(6.6) | 89(86) |
| 3 | 1.32 | 107.5 | 63 | 5.0(6.6) | 77(78) |

The IP values listed measure the ion permeability of a particular contact lens when contacted with salt ions and water. In other words, the IP value measures the ability of ions to diffuse through the contact lens. This test is more specifically described in U.S. Pat. No. 5,760,100 to Nicolson et al. The Dk value is generally a measure of the ability of a gas, such as oxygen, to diffuse through a contact lens. A more detailed description of the Dk value can also be obtained by reference to U.S. Pat. No. 5,760,100 to Nicolson et al.

In addition to the above parameters, the average contact angles (Sessle Drop) were also measured using a VCA 2500 XE contact angle measurement device from AST, Inc., located in Boston, Mass. The contact angles generally measure the surface energy of a contact lens. Furthermore, as indicated above, the NISDT, or non-invasive surface drying time, was also determined. The NISDT is a measure of the "break up time" of a particular contact lens. In particular, each contact lens was visually observed while being worn via a slit lamp, a commonly used measuring device. The NISDT was determined at the point the first disruption of the tear film was observed. Subjective results were also determined from the test subjects as to the comfort of each lens. As can be seen from Table 1, no significant differences existed in NISDT between the plasma treated lenses and the lenses of lots 1,2, and 3. Moreover, no significant differences existed in subjected comfort. The remaining parameters for the three lots were substantially comparable to each other.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A method of coating a polymeric substrate comprising the steps of:
    forming a solution, said solution containing a negatively charged material and a positively charged material in an amount such that the molar charge ratio of said solution is from about 3:1 to about 100:1;
    maintaining the pH of said solution within a range so that said negatively charged material and said positively charged material remain stable within said solution; and
    applying said solution to said substrate to form a coating thereon, said coating on said substrate having at least two layers so that one of said layers comprises said negatively charged material and another of said layers comprises said positively charged material.

2. A method as defined in claim 1, wherein said molar charge ratio is about 10:1.

3. A method as defined in claim 1, wherein said negatively charged material comprises a polyanionic material.

4. A method as defined in claim 3, wherein said polyanionic material comprises a polyacrylic acid.

5. A method as defined in claim 1, wherein said negatively charged material comprises a polyanionic material.

6. A method as defined in claim 5, wherein said polycationic material comprises poly(ethyleneimine).

7. A method as defined in claim 1, wherein said solution comprises a polyanionic material and a polycationic material.

8. A method as defined in claim 7, wherein said polyanionic material predominates said solution.

9. A method as defined in claim 7, wherein said polycationic material predominates said solution.

10. A method as defined in claim 1, wherein the pH of said solution is maintained within about ±0.5 of an appropriate pH range, said appropriate pH range being dependent on the selection of said negatively charged material and said positively charged material.

11. A method as defined in claim 10, wherein the pH of said solution is maintained within about ±0.1 of said appropriate pH range.

12. A method as defined in claim 1, further comprising the step of preconditioning said substrate before dipping said substrate into said solution.

13. A method as defined in claim 12, wherein said substrate is preconditioned with a primer coating, said primer coating being applied to said substrate by dipping said substrate into a solution containing primer materials.

14. A method as defined in claim 1, wherein the thickness of said coating is from about 40 angstroms to about 2000 angstroms.

15. A method as defined in claim 1, wherein said substrate is dipped into said solution such that a coating forms thereon.

16. A method as defined in claim 15, wherein said substrate is coated with said solution in one dip.

17. A method as defined in claim 15, where said substrate is coated with said solution in 2 to 5 dips.

18. A method as defined in claim 1, wherein said substrate comprises a mold and further comprising the steps of:
    dispensing a polymeric material into said mold;
    curing said polymeric material so that said coating detaches from said mold during curing and at least partially attaches to the exterior surface of said polymeric material; and
    removing said cured polymeric material from said mold, said polymeric material being coated with at least a portion of said solution.

19. A method as defined in claim 18, further comprising the step of preconditioning said mold with a primer coating.

20. A method as defined in claim 1, wherein said coating has at least two layers such that one of said layers consists essentially of said negatively charged material and another of said layers consists essentially of said positively charged material.

21. A method of coating a contact lens comprising the steps of:
    forming a polyionic solution, said solution containing a polyanionic material and a polycationic material in an amount such that the molar charge ratio of said solution is less than about 10:1;
    maintaining the pH of said solution within a range so that said polyanionic and polycationic materials remain stable within said solution; and
    dipping said contact lens into said solution to form a hydrophilic coating thereon, said coated substrate having at least two layers such that one of said layers comprises said polyanionic material and another of said layers comprises said polycationic material.

22. A method as defined in claim 21, wherein said polyanionic material predominates said solution.

23. A method as defined in claim 21, wherein said polycationic material predominates said solution.

24. A method as defined in claim 21, wherein the pH of said solution is maintained within about ±0.5 of an appropriate pH range, said appropriate pH range being dependent on the selection of said polyanionic material and said polycationic material.

25. A method as defined in claim 24, wherein the pH of said solution is maintained within about ±0.1 of said appropriate pH range.

26. A method as defined in claim 21, wherein said polycationic material comprises poly(ethyleneimine).

27. A method as defined in claim 21, wherein said polyanionic material comprises a polyacrylic acid.

28. A method as defined in claim 21, further comprising the step of preconditioning said contact lens before dipping said contact lens into said solution.

29. A method as defined in claim 28, wherein said contact lens is preconditioned with a primer coating, said primer coating being applied to said contact lens by dipping said contact lens into a solution containing said primer coating.

30. A method as defined in claim 21, wherein said contact lens is coated with said solution in less than about five dips.

31. A method of coating a polymeric material comprising the steps of:

provides a substrate;

applying a first polyionic material to said substrate, said first polyionic material having a certain charge;

applying an additive to said substrate, said additive having substantially no charge;

applying a second polyionic material to said substrate after applying said additive thereto, said second polyionic material having a charge opposite to said charge of said first polyionic material;

applying a solution to said substrate to form a coating thereon, said solution containing a polyanionic material and a polycationic material in an amount such that the molar charge ratio of said solution is from about 3:1 to about 100:1, wherein the pH of said solution is maintained within a range so that said polyanionic material and said polycationic material remain stable within said solution; and said coated substrate having at least two layers such that one of said layers comprises said polyanionic material and another of said layers comprises said polycationic material, said two layers substantially entrapping said additive on said coated substrate.

* * * * *